US012766212B2

(12) United States Patent
Chao

(10) Patent No.: US 12,766,212 B2
(45) Date of Patent: Oct. 20, 2026

(54) STRUCTURE OF OIL CONTROL PUMP AROMA DEVICE

(71) Applicant: Majestic-M&A International Co., Ltd., Taipei (TW)

(72) Inventor: Hsuan-Yu Chao, Taipei (TW)

( * ) Notice: Subject to any disclaimer, the term of this patent is extended or adjusted under 35 U.S.C. 154(b) by 370 days.

(21) Appl. No.: 18/640,602

(22) Filed: Apr. 19, 2024

(65) Prior Publication Data

US 2025/0325725 A1 Oct. 23, 2025

(51) Int. Cl.
*A61L 9/14* (2006.01)

(52) U.S. Cl.
CPC ........... *A61L 9/14* (2013.01); *A61L 2209/133* (2013.01); *A61L 2209/134* (2013.01)

(58) Field of Classification Search
CPC ................. A61L 9/14; A61L 2209/133; A61L 2209/134; A61L 2209/11; A61L 2209/132
See application file for complete search history.

(56) References Cited

U.S. PATENT DOCUMENTS

2023/0264221 A1* 8/2023 Chang ................. B05B 17/0615 239/102.2

* cited by examiner

*Primary Examiner* — Brendan A Hensel

(57) ABSTRACT

An improved structure of oil control pump aroma device primarily comprises: an outer shell main body, a universal adapter, a control oil pump, a misting oil tank, a control circuit, and a fan. The universal adapter serves as a magnetic movable joint for locking commercially available essential oil bottles, while a magnetic oil supply interface is recessed on the top of the outer shell main body to facilitate assembly and removal of the universal adapter with essential oil bottles. During operation, the control oil pump is controlled by an electromagnetic switch to inject essential oil into the misting oil tank, where it is atomized by an ultrasonic atomizer, and finally diffused into the external air by a fan. The overall effective design enables users to select their favorite fragrance according to their preferences, thereby achieving practical purposes such as relieving tension and improving air quality.

5 Claims, 5 Drawing Sheets

100

STRUCTURE OF OIL CONTROL PUMP AROMA DEVICE

FIELD OF THE INVENTION

The present invention relates to the technical field of aroma devices, particularly to an improved structure of oil control pump aroma device.

THE PRIOR ARTS

In recent years, the medical and beauty industries have rapidly developed, with increasing emphasis on beauty care and medical health. For example, ultrasonic water oxygen machines, beauty and health care machines, water mist aroma humidifiers, essential oil diffusers, etc., are widely used in beauty salons and ordinary households. They mainly use the principle of ultrasonic atomization to atomize fragrance liquids into fine mist particles, which are then diffused into the surrounding environment.

However, conventional ultrasonic aroma diffusers generally require transferring fragrance from commercially available containers to dedicated containers before used, which is inconvenient. Newer designs include universal essential oil diffusers that allow commercially available essential oil bottles to be directly screwed onto the diffuser's spray universal adapter, eliminating the need for additional purchases or transfers, making aromatherapy convenient.

Although these new designs are convenient to use, the spray universal adapter lacks good ventilation design, resulting in negative pressure buildup after continuous spraying, leading to blockages in the liquid supply and inefficient spraying. Additionally, to save costs, the back of the atomizing sheet is usually directly attached to the end of the oil supply channel, with no good anti-leakage measures between the atomizing sheet and the oil supply channel. However, due to the lack of surface tension of essential oils, leakage can occur easily, leading to unnecessary waste when the bottle is inverted after filling.

Furthermore, existing universal essential oil diffusers have imperfect structural designs, making it difficult to control the amount of essential oil dispensed. Additionally, most of them only have a single universal adapter on the outer shell, allowing only one type of essential oil bottle to be assembled at a time. When changing to a different fragrance, users have to unscrew and reinstall another essential oil bottle, which is inconvenient and requires repeated operations.

SUMMARY OF THE INVENTION

In view of the foregoing, the main object of the present invention is to provide an improved structure of oil control pump aroma device, primarily comprising: an outer shell main body with a universal adapter on top for locking commercially available essential oil bottles. Below the universal adapter is a control oil pump to control its oil output, connected to a misting oil tank via a pipeline. The misting oil tank is equipped with an ultrasonic atomizer at the bottom to provide essential oil atomization. A control circuit electrically connected to a rechargeable battery pack and a switch, and electrically controlling the conduction operation of the control oil pump, the ultrasonic atomizer, and a fan, with spray released to the outside through an obliquely extending spray outlet. The features are:

The universal adapter is a magnetic movable joint, composed of a bottle cap upper shell and a bottle cap lower shell with a plurality of neodymium magnets fixed in the middle. The bottle cap lower shell is annular with spaced holes for placing the neodymium magnets, and the bottle cap upper shell is composed of a threaded interface with a centrally recessed center, in which a sealing rubber pad is provided.

A magnetic oil supply interface is recessed on the top of the outer shell main body, with multiple neodymium magnets spaced apart on the inner shell of the magnetic oil supply interface. This allows the magnetic attraction assembly of the universal adapter and convenient assembly and removal, as well as retrieval, of essential oil bottles.

The control oil pump is controlled by an electromagnetic switch, with an outer shell provided with an inlet short pipe and an inlet sealing ring at the upper inlet end to connect to the magnetic oil supply interface, and a lower outlet end provided with an L-shaped pipe to connect to the misting oil tank.

Compared with existing known structures, the advantages of the improved structure of the oil control pump aroma device of the present invention lie in the fact that the universal adapter adopts a magnetic movable joint, which facilitates assembly and removal, enabling multiple backups to be available for convenient interchange of different essential oil combinations. During operation, the control oil pump is controlled by an electromagnetic switch to inject essential oil into the misting oil tank, where it is atomized by an ultrasonic atomizer, and finally diffused into the external air by a fan. The overall effective design enables users to select their favorite fragrance according to their preferences, thereby achieving practical purposes such as relieving tension and improving air quality.

DETAILED DESCRIPTION OF PREFERRED EMBODIMENTS

Figure 1:
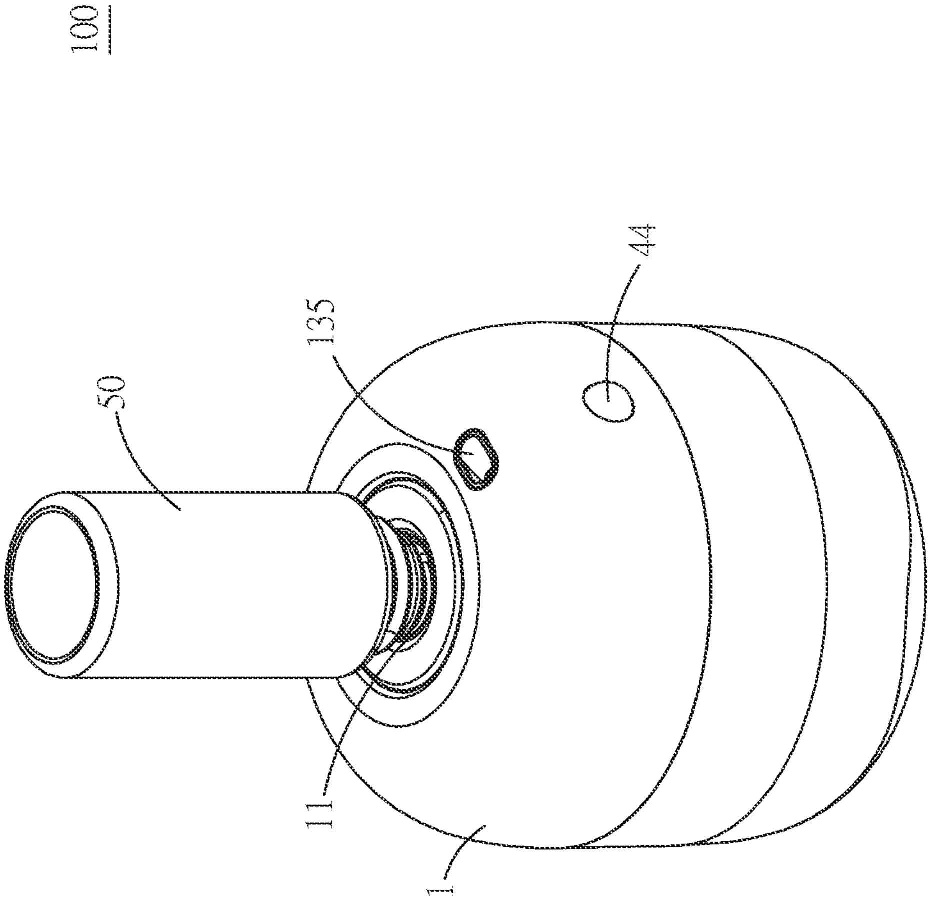
FIG. 1 is a three-dimensional assembly diagram of the present invention.
Figure 2:
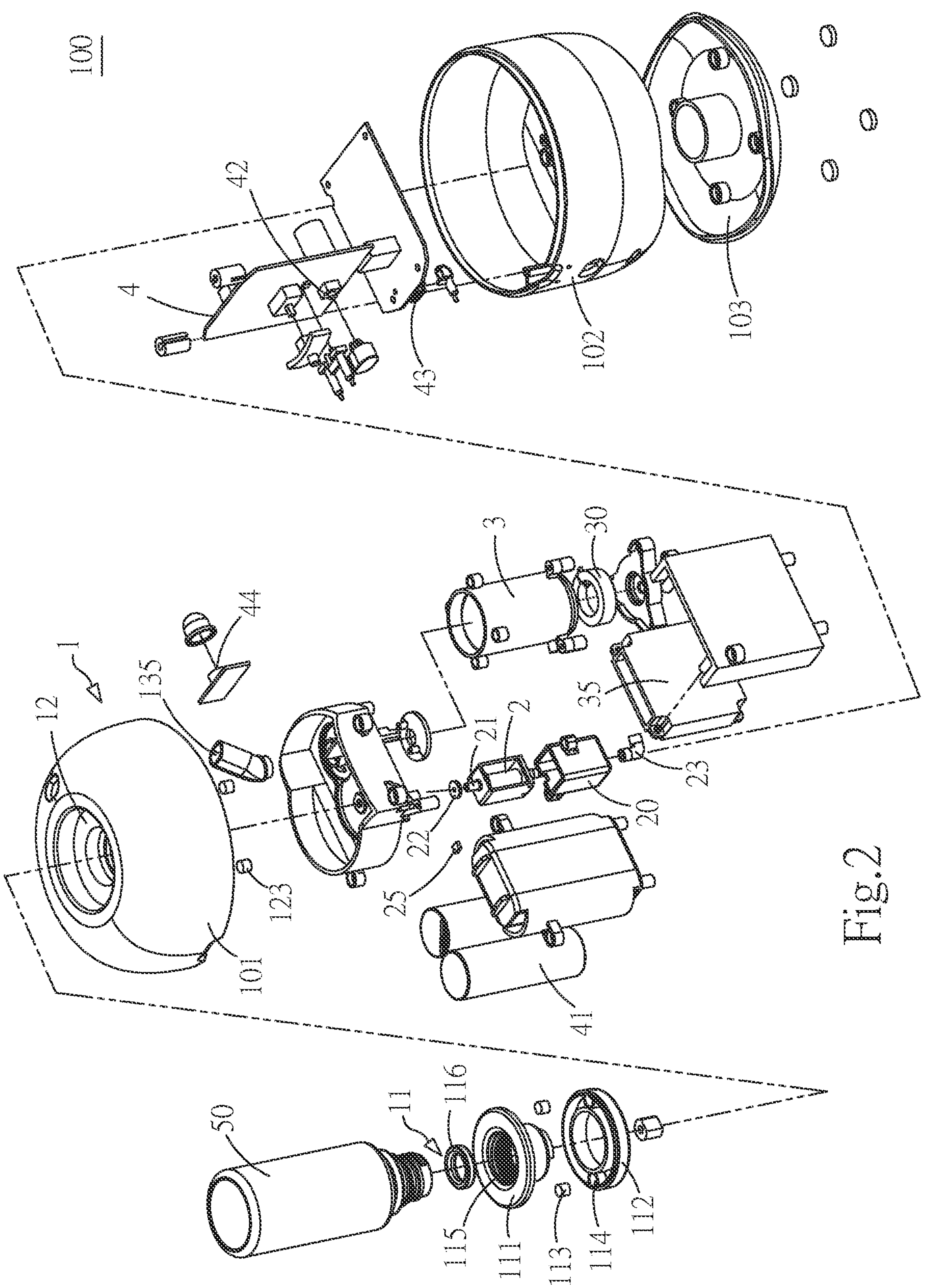
FIG. 2 is an exploded three-dimensional diagram of the present invention.
Figure 3:
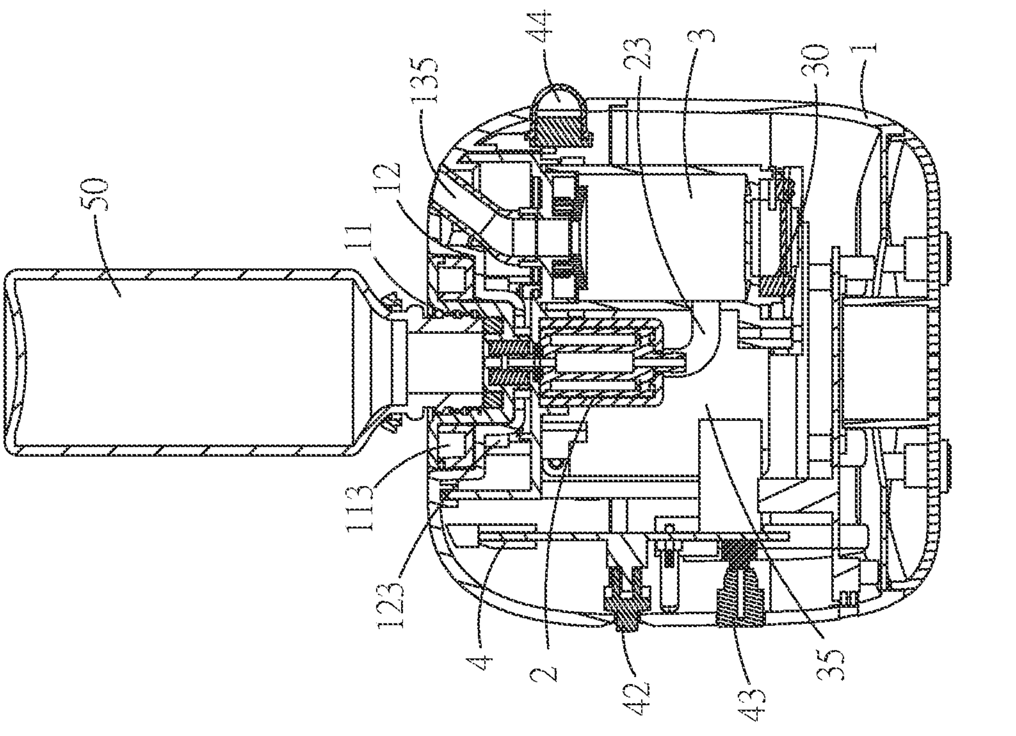
FIG. 3 is a combined cross-sectional view of the present invention.

To facilitate understanding the content of the present invention and the effects it can achieve, specific embodiments are listed with reference to the drawings. Detailed explanations are provided as follows: Please refer to FIGS. 1 through 4. The improved structure 100 of the oil control pump aroma device of the present invention mainly includes: an outer shell main body 1 on which a universal adapter 11 is provided for locking commercially available essential oil bottles 50. A control oil pump 2 is provided below the universal adapter 11 to control its oil output, is connected to a misting oil tank 3 via a pipeline. An ultrasonic atomizer 30 is provided at the bottom of the misting oil tank 3 to provide essential oil atomization. A control circuit 4 electrically connects to a rechargeable battery pack 41 and a switch 42, and electrically controls the conduction operation of the control oil pump 2, the ultrasonic atomizer 30, and a fan 35. Spray is released to the outside through an obliquely extending spray outlet 135. Its features are:

The universal adapter 11 is a magnetic movable joint, composed of a bottle cap upper shell 111 and a bottle cap lower shell 112, with a plurality of neodymium magnets 113 fixed in the middle. The bottle cap lower shell 112 is annular with spaced holes 114 on it to place the neodymium magnets 113, and the bottle cap upper shell 111 is composed of a threaded interface 115 with a centrally recessed center. A sealing rubber pad 116 is provided in the threaded interface 115.

A magnetic oil supply interface 12 is provided above the outer shell main body 1, with a plurality of neodymium magnets 123 spaced apart on the inner shell of the magnetic oil supply interface 12, allowing the magnetic attraction assembly and easy separation and removal of the universal adapter 11.

The control oil pump 2 is controlled by an electromagnetic switch 25, and the control oil pump 2 is provided with an outer shell 20. An inlet short pipe 21 and an inlet sealing ring 22 are provided at the upper inlet end to connect to the magnetic oil supply interface 12, and a lower outlet end is provided with an L-shaped pipe 23 to connect to the misting oil tank 3.

In a preferred embodiment, the control circuit 4 is further connected to a USB socket 43 and an indicator light 44 on the outer shell main body 1.

In a preferred embodiment, the outer shell main body 1 is further composed of mutually stacked upper shell 101, middle shell 102, and lower shell 103.

In a preferred embodiment, the outer shell main body 1 can be formed into different shapes, such as an elliptical sphere, spherical body, cylinder, cube, polygon, and other geometric shapes, without being limited thereto.

Figure 4:
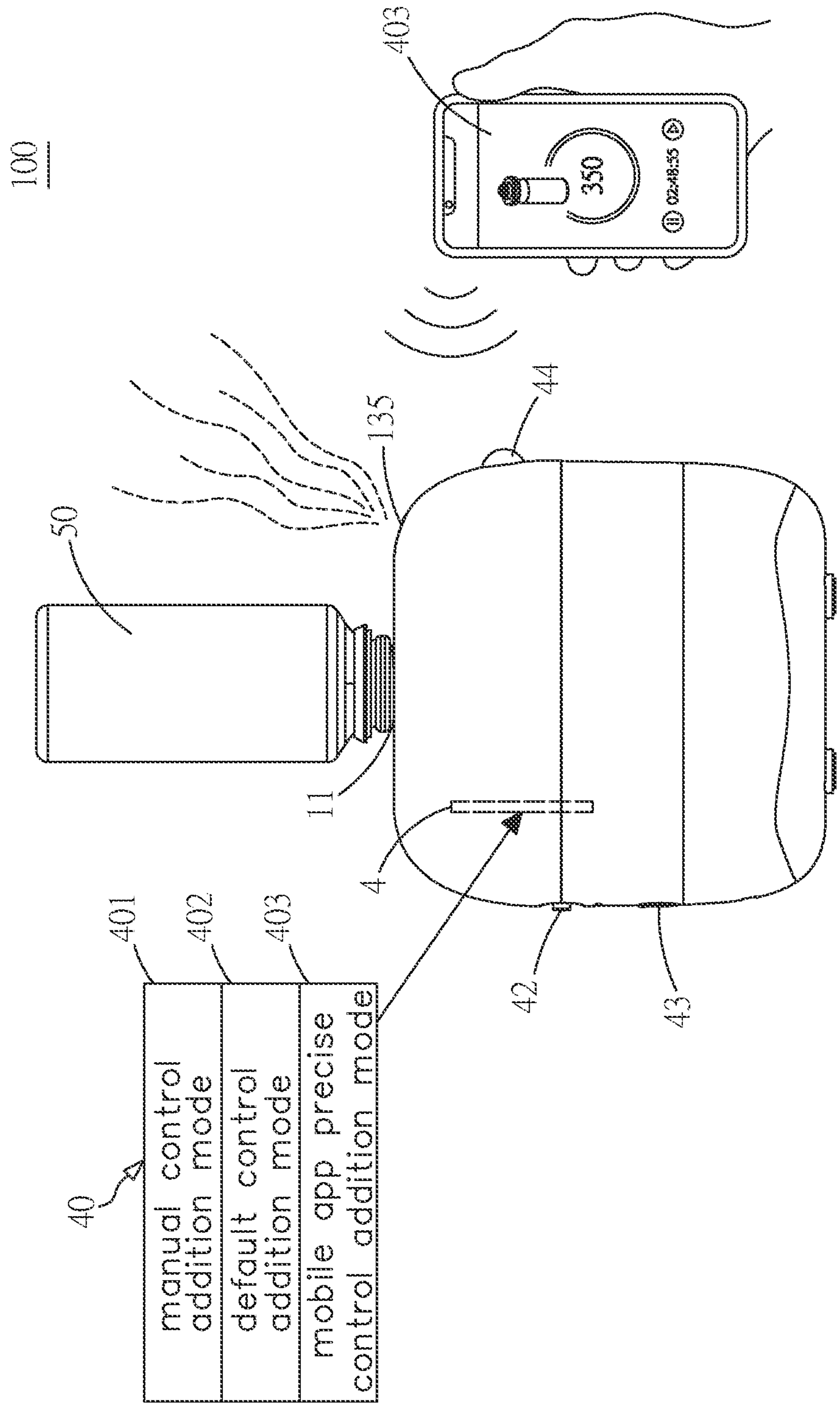
FIG. 4 is an application example diagram of the present invention.
Figure 5:
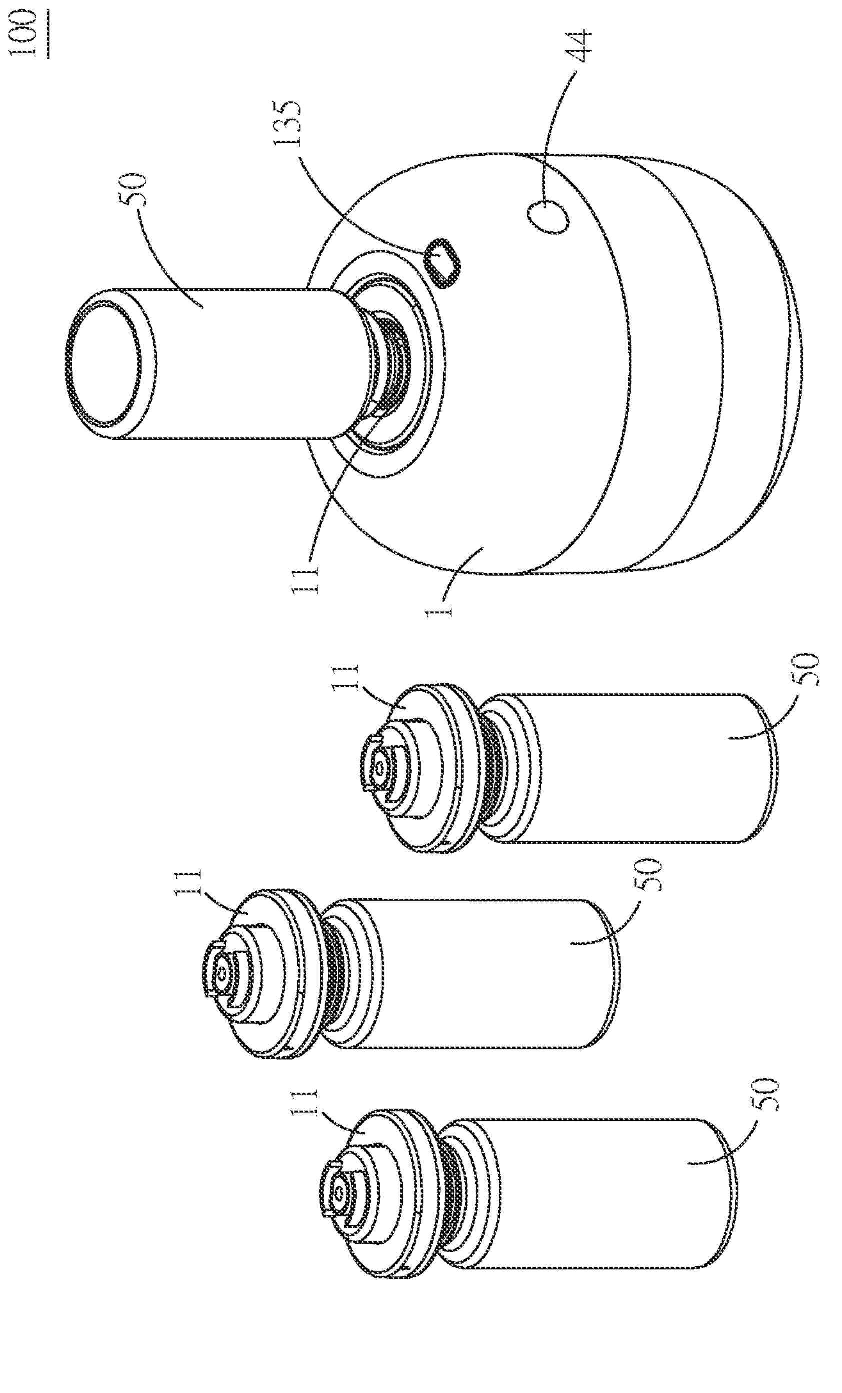
FIG. 5 is a schematic diagram illustrating the convenient replacement of different essential oil bottles of the present invention.

In a preferred embodiment, as shown in FIG. 4, the control circuit 4 further has a set mode 40, including a manual control addition mode 401, a default control addition mode 402, and a precise control addition mode 403 via a mobile app.

The present invention has the advantages that: 1. The universal adapter 11 of the present invention uses a magnetic movable joint, so it can be easily assembled and separated, allowing multiple backups for different essential oil bottles 50 to be matched and combined. Thus, it is easy to replace different essential oils.

2. The present invention uses precise oil control technology for the control oil pump 2, preventing oil leakage while adjusting the oil flow according to needs, ensuring optimal results every time and avoiding waste of essential oils.

3. The present invention uses an ultrasonic atomizer 30 combined with a fan 35, which can effectively atomize essential oils into fine mist, allowing the aroma to be more evenly distributed in the air, enhancing the absorption of essential oils by the human body, and providing the best aromatherapy effect to users.

4. The effective intelligent setting mode 40 of the control circuit 4 can provide a manual control addition mode 401, a default control addition mode 402, and a precise control addition mode 403 via a mobile app. It is easy to operate, allowing easy startup or shutdown of the device, meeting various practical needs to adjust the concentration of essential oils and the fan speed, and providing a personalized high-quality aromatic experience in life.

What is claimed is:

1. A structure of oil control pump aroma device, comprising: an outer shell main body with a universal adapter provided thereon for locking commercially available essential oil bottles, wherein a control oil pump is provided below the universal adapter to control its oil output, connected to a misting oil tank via a pipeline, with a ultrasonic atomizer provided at a bottom of the misting oil tank to provide essential oil atomization; a control circuit electrically connected to a rechargeable battery pack and a switch, and electrically controlling a conduction operation of the control oil pump, the ultrasonic atomizer, and a fan, with spray released to an outside through an obliquely extending spray outlet, characterized in that:

the universal adapter is a magnetic movable joint, composed of a bottle cap upper shell and a bottle cap lower shell with a plurality of neodymium magnets fixed in a middle, the bottle cap lower shell is annular with spaced holes for placing the neodymium magnets, and the bottle cap upper shell is composed of a threaded interface with a centrally recessed center, in which a sealing rubber pad is provided;

the outer shell main body is provided with a magnetic oil supply interface, with a second plurality of neodymium magnets spaced apart on an inner shell of the magnetic oil supply interface, allowing the magnetic attraction assembly to be separated from the universal adapter, and;

the control oil pump is controlled by a second switch, and the control oil pump is provided with an outer shell, with an inlet short pipe and an inlet sealing ring provided at an upper inlet end to connect to the magnetic oil supply interface, and a lower outlet end provided with an L-shaped pipe to connect to the misting oil tank.

2. The structure of the oil control pump aroma device as claimed in claim 1, wherein the control circuit is further connected to a USB socket and an indicator light on the outer shell main body.

3. The structure of the oil control pump aroma device as claimed in claim 1, wherein the outer shell main body is further composed of a mutually stacked upper shell, a middle shell, and a lower shell.

4. The structure of the oil control pump aroma device as claimed in claim 1, wherein the outer shell main body is formed into an elliptical sphere, a spherical body, a cylinder, a cube, a polygon, or other geometric shapes.

5. The structure of the oil control pump aroma device as claimed in claim 1, wherein the control circuit further has a setting mode, including a manual control addition mode, a default control addition mode, and a mobile app precise control addition mode.

* * * * *